United States Patent
Cortese et al.

(10) Patent No.: US 6,322,531 B1
(45) Date of Patent: *Nov. 27, 2001

(54) INSERTABLE APPLICATOR HAVING A PIVOTAL FINGER GRIP TAB

(75) Inventors: Gabriel C. Cortese, Watchung; Kelly Huang, Hillsborough, both of NJ (US)

(73) Assignee: McNeil-PPC, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/344,883
(22) Filed: Jun. 25, 1999
(51) Int. Cl.[7] ........................................ A61F 13/20
(52) U.S. Cl. ........................................ 604/15
(58) Field of Search ............... 604/11–18, 904, 604/57–60, 285–288

(56) References Cited

U.S. PATENT DOCUMENTS

| | | | |
|---|---|---|---|
| 2,587,717 | * 3/1952 | Fourness | 604/14 |
| 3,090,385 | * 5/1963 | Brecht | 604/14 |
| 3,534,737 | * 10/1970 | Jones, Sr. | 604/15 |
| 4,573,963 | 3/1986 | Sheldon | 604/15 |
| 4,891,042 | * 1/1990 | Melvin et al. | 604/18 |

FOREIGN PATENT DOCUMENTS

| | | |
|---|---|---|
| 0 373 296 A1 | 6/1990 | (EP) . |
| 532 745 a | 1/1941 | (GB) . |

* cited by examiner

Primary Examiner—Dennis Ruhl

(57) ABSTRACT

The present invention relates to applicators for delivering objects into a body cavity, having a pivotal finger grip tab to improve the ability of a user to maintain a secure grip on the applicator during use. Prior to use the tab can reside in a first position that is proximal the applicator outer surface. When a user is ready to insert the applicator into a body cavity, the tab is pivoted outwardly to a second position distal the applicator outer surface. The tab in its outwardly pivoted second position provides a surface for a user's finger and/or thumb to apply a force that is parallel to the length of the applicator instead of perpendicular (normal force) to the applicator. Thus minimizing the opportunity for applicator failure and resistance to material expulsion as a result of increased friction on the material itself or an optional expulsion member.

26 Claims, 5 Drawing Sheets

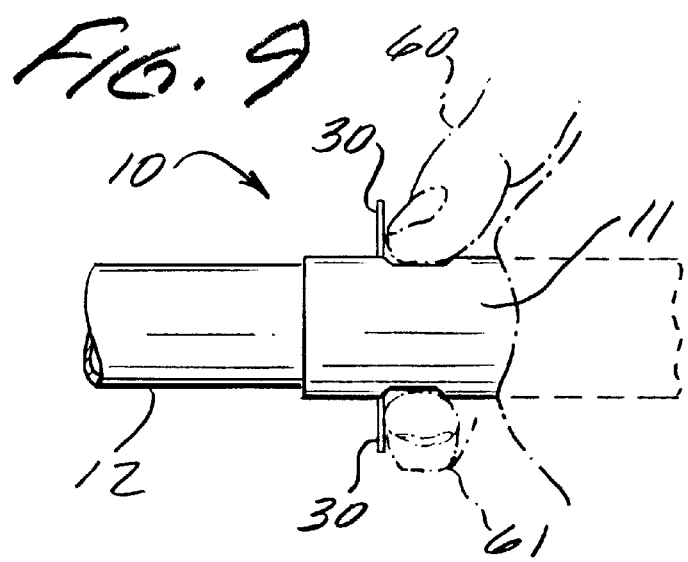
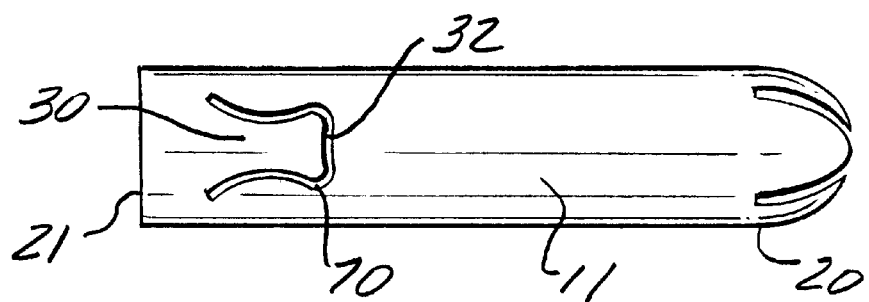
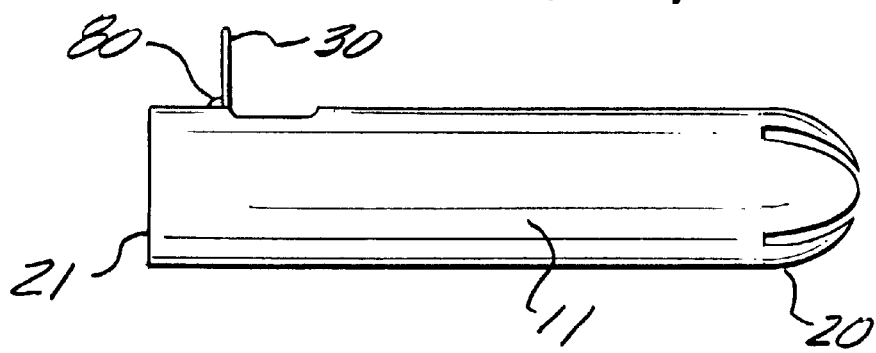

INSERTABLE APPLICATOR HAVING A PIVOTAL FINGER GRIP TAB

FIELD OF THE INVENTION

The present invention relates to applicators for delivering materials into a body cavity, having a pivotal finger grip tab to improve the ability of a user to maintain a secure grip on the applicator during use.

The applicator is particularly useful for delivering catemenial devices into the vaginal canal.

BACKGROUND OF THE INVENTION

Applicators for delivering materials into a body cavity typically comprise an insertion member having an 15 insertion end and a gripper end opposite thereof, and an expulsion member slideably fitted within the insertion member. The gripper end will generally incorporate features to allow a user to more or less securely hold the applicator during use, which includes the following steps: inserting the applicator into a body cavity, expelling a substantially enclosed material contained by the applicator, and withdrawing the applicator from the body.

Attempts have been made to improve the user's ability to manipulate the applicator during use. One approach is to significantly reduce the diameter of the applicator in the gripper end, as can be seen in Whitehead, U.S. Pat. No. 4,508,531. A disadvantage to this approach is while a reduced diameter grip may help in preventing fingers from slipping during insertion, there is little or no resistance offered in the opposite direction during the expulsion step. This is a step with which many users have difficulty.

Another approach to improve the grip of the applicator during use is to incorporate projections, such as in the form of a ring, at the base of the applicator member being inserted into the body. Examples of this approach are disclosed in Voss, U.S. Pat. No. 4,361,150, and in Sartinoranont, U.S. Pat. No. 4,447,222. In order for the projections to function as intended, they must be of significant dimension. However, a number of disadvantages are realized as the projection dimensions increase. One disadvantage is the handling of the applicators during high-speed manufacturing. Applicators are transferred from one position to another many times throughout their manufacture, and the projections can become snagged, severely affecting the output efficiency and quality of the products. Many high-speed manufacturing processes include at least one buffering system that accumulates materials and products between major steps of manipulation and assembly. Applicators with projections generally do not stack neatly (parallel) in the buffering systems. This negatively affects the efficiency of space and transfer, and it potentially creates jams in the process due to applicators being "hung up" in the accumulators or interconnected with adjacent applicators.

A second disadvantage of applicators having projections is related to the packaging of the fully assembled applicators. Just as the applicators will not stack neatly in the buffering systems of high-speed manufacturing equipment, the applicators will not stack neatly in a package of two or more. Either extra packaging material is needed to compensate for non-parallel stacking, or additional equipment and processing steps is required to orient adjacent applicators such that the projections are opposite one another.

Yet another approach to improve the handling of applicators is to increase the friction in the gripper end. This is especially true, as tampon manufacturers are moving toward the use of higher gloss surfaces, which are purported to aid in ease of applicator insertion into a body cavity. An example of this approach is disclosed in Voss, U.S. Pat. No. 3,575,169, wherein an applicator is coated with pulverized stone or sand.

Hagerty, U.S. Pat. No. 5,709,652, discloses an applicator having a plurality of finger-accepting apertures to provide relatively abrupt, finger-accepting edges to frictionally resist movement of a user's finger in response to longitudinal forces on the device. Although a useful contribution to the art, the finger-accepting edges of Hagerty, are limited to the wall thickness of the tubular element.

With many of gripping features described heretofore, the natural tendency of a user is to maximize the friction by applying an increasingly greater normal force, which may result in applicator failure. This failure can be two-fold: one, the applicator can collapse under the normal force and two, the applicator insertion member can increase the amount of friction on an expulsion member slideably fitted within the insertion member, resulting in the inability to expel the material contained by the applicator.

In view of the shortcomings of the prior art, what is needed is an applicator which has substantial resistance to finger slip during use, minimizes applicator collapse and failure, is conducive to high-speed manufacturing, and is conducive to efficient packaging.

SUMMARY OF THE INVENTION

The present invention relates to an applicator for delivering an object into a mammalian body cavity having at least one pivotal finger grip tab located on an elongate insertion member, to provide a user with a secure hold during the insertion, expulsion, and withdrawal steps of applicator use. Prior to use the tab can reside in a first position that is proximal the applicator outer surface, resulting in improvements over the stated disadvantages of the prior art; in particular, during the manufacture and packaging of the applicators. When a user is ready to insert the applicator into a body cavity, the tab is pivoted outwardly to a second position distal the applicator outer surface. The tab in its outwardly pivoted second position provides a bearing surface for one or more of a user's manual digits (fingers and thumb) to apply a force that is parallel to the length of the applicator instead of perpendicular (normal force) to the applicator. This minimizes increased friction caused by collapsing the finger grip portion of the tubular insertion member against the insertable object and/or an optional expulsion member.

BRIEF DESCRIPTION OF THE DRAWINGS

FIG. 9 is a side view of an applicator according to the present invention while in use.

FIG. 10 is a side view of a tubular insertion member having a formed tab in the gripper end and having an optional gap between the edges of the tab and the surrounding area of the tubular insertion member.

FIG. 11 is a side view of a tubular insertion member having an optional protuberance positioned adjacent a tab fixed end for restricting the angle of tab rotation.

DETAILED DESCRIPTION OF THE INVENTION

Figure 1:
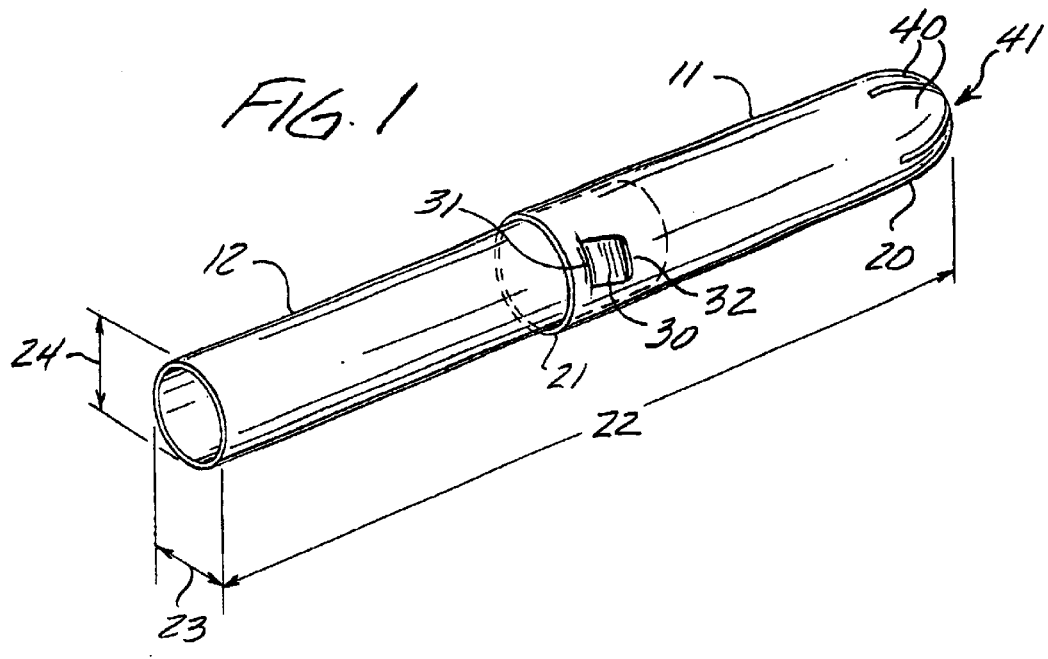
FIG. 1 is a perspective view of an applicator according to the present invention.
Figures 2A, 2B, 2C:
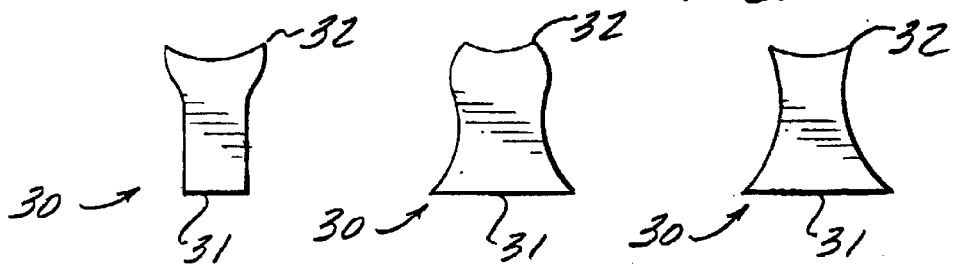
FIGS. 2A–2G are front views of finger grip tabs having various geometric patterns as provided by the present invention.
Figures 2D, 2E, 2F, 2G:
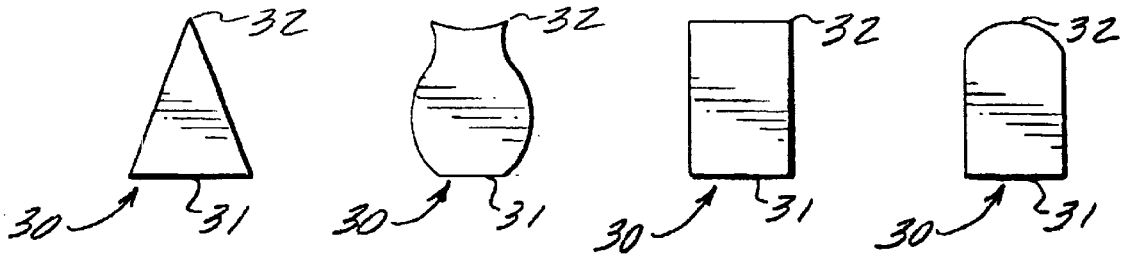

The following is a detailed description of the present invention, wherein like elements are labeled with like numerals in FIGS. 1–11. Referring to FIG. 1, one embodiment of the present invention relates to an applicator 10 comprising a tubular insertion member 11 and an expulsion member 12 as prepared for use in expelling its contained material. The tubular insertion member 11 comprises an insertion end 20, a gripper end 21, a length 22 that runs from the insertion end 20 to the gripper end 21, and a tab 30 pivotally connected to the tubular insertion member 11 in the gripper end 21. The tab 30 has a fixed end 31 where it is connected to the tubular insertion member 11, and a free end 32 that can pivot about the fixed end 31. The insertion end 20 may have a plurality of inwardly curved petals 40 forming a substantially closed dome 41.

The tab 30 is illustrated perpendicular to the length 22 of the applicator 10. The tab 30 can take this orientation by pivoting it in an arc from an original orientation parallel to the length 22 of the applicator 10.

The tab may take essentially any desired shape including triangles, ovals, rectangles, bulbs, tear-drops, having flared free ends, or having flared fixed ends, and other various geometric patterns. Representative, non-limiting examples of useful geometric patterns for the tab 30 are illustrated in FIGS. 2A–2G.

Figure 3:
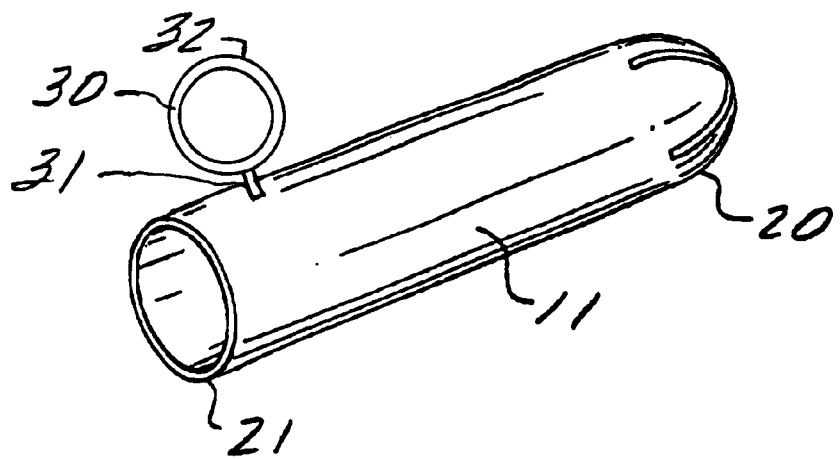
FIG. 3 is perspective view of a tubular insertion member having a ring-shaped tab pivotally connected thereon.

FIG. 3 depicts an embodiment of the present invention having a ring-shaped tab 30'. The ring-shaped tab 30' is configured and dimensioned to accept a least a portion of a user's manual digit(s). As an added convenience, a tab 30' in the form of a ring would allow a user to essentially have both hands free during the many steps involved in removing and disposing of a soiled tampon and insertion of a subsequent tampon. In contrast to the tab 30 of FIG. 1, the tab 30' of FIG. 3 is pivotable from an original orientation substantially perpendicular to the length of the applicator.

The tubular insertion member has at least one tab.

Figure 4:
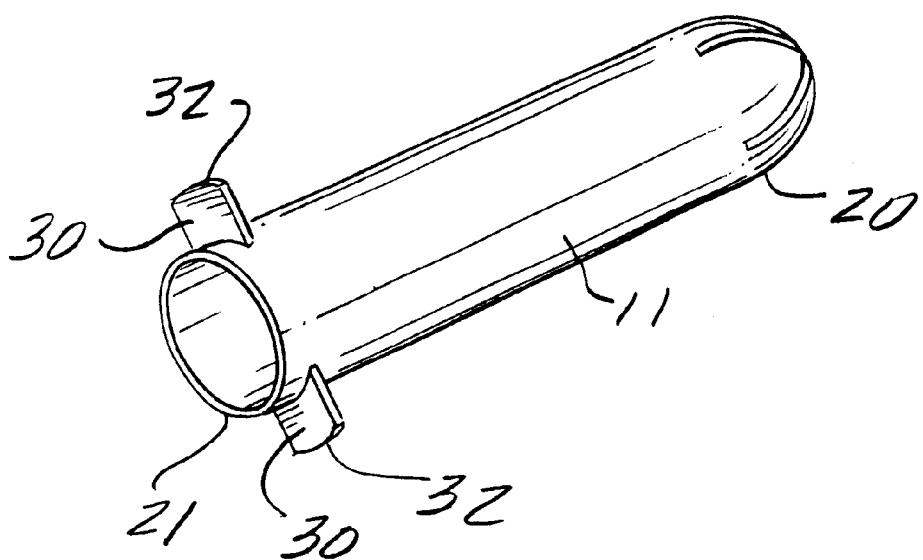
FIG. 4 is a perspective view of a tubular insertion member having two finger grip tabs in an outwardly pivoted position.

Preferably, it contains a plurality of tabs disposed about the circumference of the gripper end. A preferred embodiment is illustrated in FIG. 4, in a side view depicting a first and second tab 30 positioned approximately 180° from one another. FIG. 4 shows the tab free ends 32 in an outwardly pivoted position distal the outer surface of the tubular insertion member 11.

Figure 5:
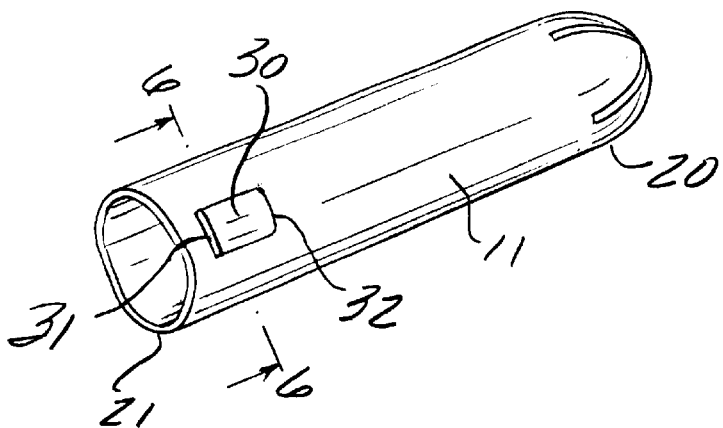
FIG. 5 is perspective view of a tubular insertion member having a finger grip tab pivotally attached thereto.
Figure 6:
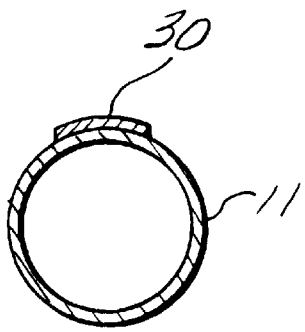
FIG. 6 is a cross section taken through line 6—6 of FIG. 5, depicting a pivotally attached tab in a first position substantially radially symmetric with the tubular insertion member.

FIGS. 5 through 8 are useful in illustrating the differences in connecting tab 30 to insertion member 11 according to the present invention. As can be seen in FIGS. 5 and 6, tab 30 is an additional and separate element to that of the tubular insertion member 11. Tab 30 can be formed during the formation of the tubular insertion member 11, such as by an injection molding process, or formed separately and then joined to the tubular insertion member 11 in a separate processing step, such as by the use of adhesives, ultrasonic welding, or heat sealing.

Figure 7:
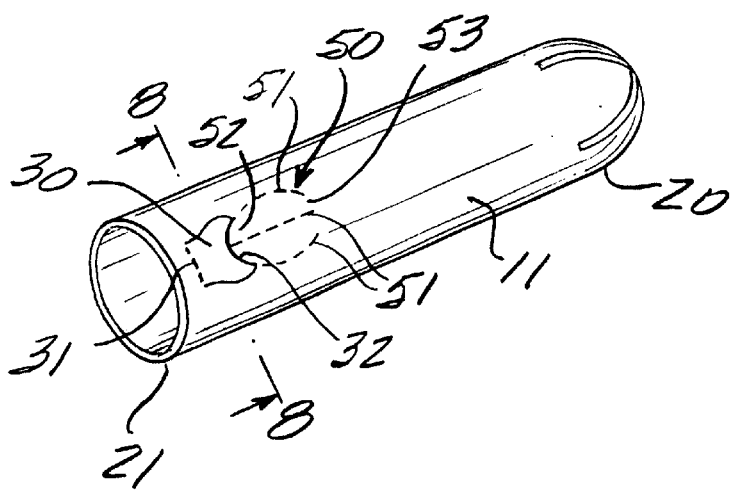
FIG. 7 is a perspective view of a tubular insertion member having a formed tab in the gripper end of a tubular insertion member, as well as an optional weakened region adjacent the formed tab.
Figure 8:
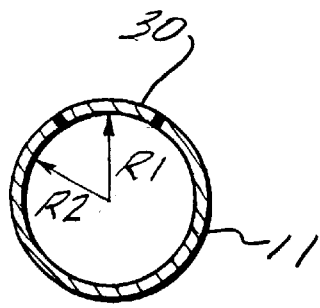
FIG. 8 is a cross section taken through line 8—8 of FIG. 7, depicting the formed tab in a first position radially symmetric with the tubular insertion member.
Figure 7A:
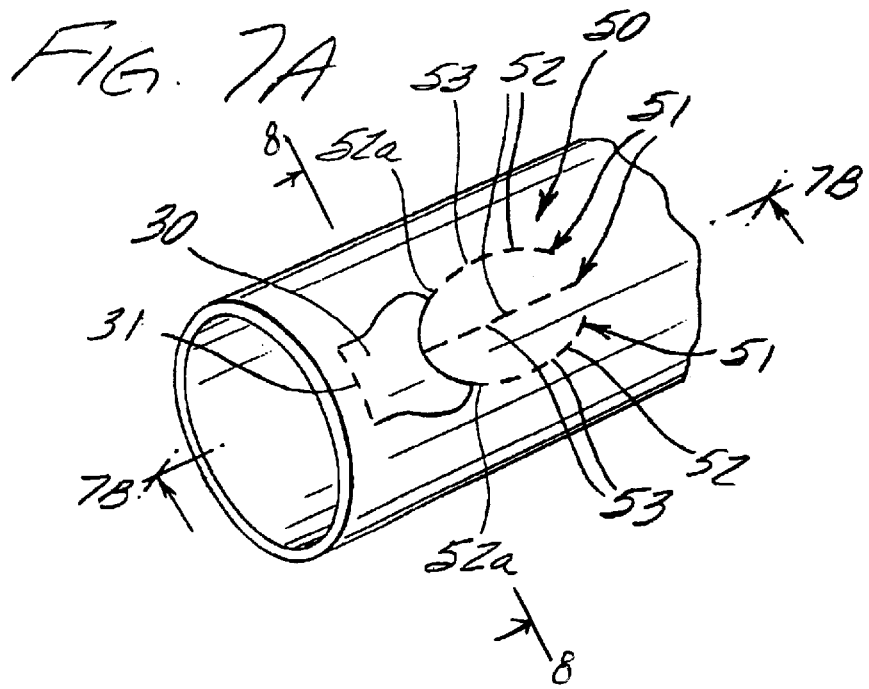
FIG. 7A is an enlarged view of the finger grip portion of the applicator of FIG. 7.
Figure 7B:
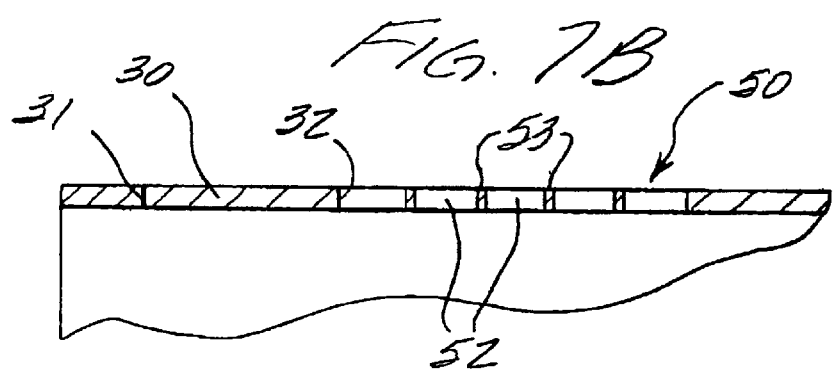
FIG. 7B is a partial cross-section taken through line 7B—7B of FIG. 7A.
Figure 7C:
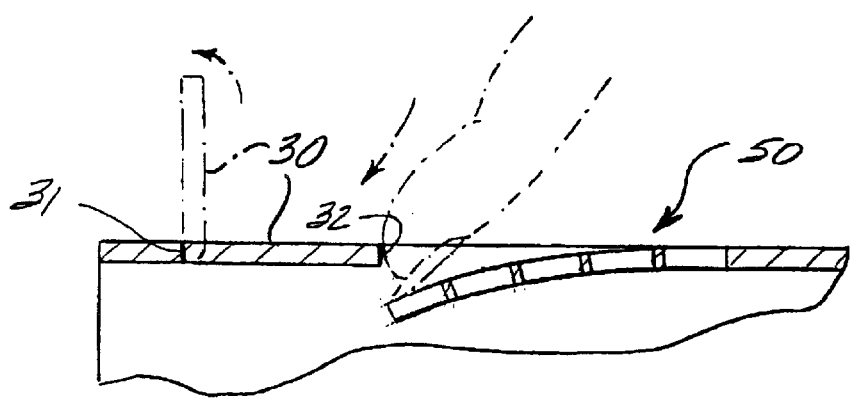
FIG. 7C illustrates a user's manipulation of the finger grip depicted in FIG. 7B.

FIGS. 7–7C and 8 depict a tubular insertion member 11 having a tab 30 formed directly in the gripper end 21. The tab 30 is integrally connected to the insertion member 11 by completely cutting through the wall of the tubular insertion member 11 along at least portions of the periphery of the tab 30, leaving a fixed end 31. A representative, non-limiting list of methods useful for defining the tab 30 by a line of separation in the tubular insertion member wall is the following: die-cutting, laser cutting, water jet cutting, thermoforming, grinding, and the like.

FIGS. 7, 7A, 7B and 8 depict the formed tab 30 in a first position that has substantially the same elevation as portions of the insertion member 11 surrounding the tab prior to use. As used herein, the phrase "substantially the same elevation" and modifications thereof include co-planar, having the same radius (as in FIG. 8), and having a thin member attached to or extending from the surface (as in FIG. 6). In a preferred embodiment, wherein the insertion member 11 is tubular (as in FIG. 8), the tab 30 is radially symmetric to the surrounding area of the tubular insertion member 11. In other words, the radial distance R1 from a center point is substantially equal to the radial distance R2. This is the position of the tab 30 during manufacturing, assembly, and packaging, thereby providing several benefits. In the radially symmetric position, the applicator can be processed on high-speed equipment, capable of enduring a plurality of transfer points in any direction without snagging and creating jams. Additionally, the applicators will stack in a substantially parallel fashion in accumulating reservoirs that typically accompany state of the art processing equipment (see U.S. Pat. No. 4,755,164). If the tab free ends were pivoted outwardly to a second position during manufacture and assembly, then the applicators would "fan" in two directions in the reservoirs as a result of non-parallel stacking, potentially resulting in transfer failures due to applicator jams and/or interconnected adjacent applicators.

FIG. 7 depicts the tab fixed end 31 as a perforated line. Preferably, the perforated line has a radius corresponding to the radius of the tubular insertion member 11 to account for the tube curvature when tab 30 is pivoted outwardly. Fixed end 31 may optionally be a scored or perforated line, thereby reducing the amount of force required to outwardly pivot tab free end 32 from its initial radially symmetric position to a second position that is distal the outer surface of the tubular insertion member 11.

As shown in FIG. 7C, when a consumer is ready to use the applicator, she simply pivots the tab free end 32 from its initial radially symmetric position to an outward second position that is distal the outer surface of the tubular insertion member. The user grasps the applicator in the gripper end with one or two hands, utilizing the tab to provide resistance to finger slip during applicator insertion, material expulsion, and applicator withdrawal. FIG. 9 illustrates an applicator 10 of the present invention in use, with a user's thumb 60 residing on a first tab 30, and a finger 61 residing on a second tab 30, which is approximately oppositely disposed about the circumference of the tubular insertion member 11.

Referring to FIGS. 7A and 7B, a region of weakness 50 adjacent the tab free end 32 can optionally be employed to further enable a user to position a finger and/or thumb underneath the tab free end 32 for pivoting the tab 30 outwardly to its useable position as shown in FIG. 7C. The region of weakness 50 will allow the tubular insertion member 11 in that region to be inwardly displaced. Preferably the region of weakness 50 comprises scored or perforated lines adjacent the tab free end 32. As used herein, scored is defined as a partial cut (less than 100 percent) through the thickness of the tubular insertion member. Perforated is defined as a line of holes with uncut or scored material residing between the holes. The dimension and geometry of the holes can vary, as well as the dimension of the uncut material therebetween. FIGS. 7A and 7B illustrate a preferred arrangement of the region of the weakness 50 including a series of perforated lines 51 having perforated components 52 and land components 53, with terminal perforated components 52a most proximal the tab free end 32 adjoining the tab free end 32. This helps to increase the inward displacement of weakened region 50, thereby providing sufficient space to fit a portion of a user's finger/thumb underneath the tab free end 32.

FIG. 10 illustrates an optional gap 70 between the is edges of the tab 30 and the tubular insertion member 11 surrounding the tab 30. This gap 70 can also aid a user in positioning a thumb or finger underneath the tab free end 32 for pivoting the tab 30 outwardly to its useable position. The gap 70 may be positioned along the entire tab periphery (excluding the fixed end 31) or alternatively in select areas. The dimensions of the gap width is from about 0.5 to about 3.0 millimeters, preferably between 0.75 and 1.25 millimeters. This gap width may serve to relieve material stress during pivoting of the tab to avoid tearing the material. The edges may also be substantially abutted, in an effort to maintain the hygienic state of the material contained by the applicator.

Referring to FIG. 11, it is preferred that the tab free end 32 is pivoted outwardly approximately 90° from its initial position, radially symmetric to the outer surface of the tubular insertion member. This preferred position provides the maximum amount of resistance to finger slip during use of the applicator 10. To restrict the angle of pivot, one or more protuberances 80 can optionally be employed adjacent the fixed end 31 of the tab 30. The protuberances 80 may take the form of bumps, pyramids, rings, and the like.

The applicators of the present invention can be made of any useful materials. Generally, materials known to those of ordinary skill in the art include plastics (polymers) and cardboard. The plastic is applicators may be of conventional polymers, such as polyolefins, or be of more sophisticated polymers and polymer blends formulated to provide features such as biodegradability and/or water dispersibility. Examples of applicators that are designed to be dispersible or biodegradable are disclosed in U.S. Pat. Nos. 5,002,526 and 5,782,794 (relating to applicators made from polyvinyl alcohol based compositions), U.S. Pat. No. 5,350,354 (relating to applicators made from starch based compositions), and U.S. Pat. No. 4,900,299 (relating to applicators made from poly(3-hydroxybutyric acid) based compositions). Plastic applicators are often made by the following non-limiting processes: injection-molding, blow-molding, and extrusion.

Cardboard applicators can be constructed from a single layer of cardboard material, or from a plurality of laminated layers to provide benefits relating to the various layers. Useful cardboard stock for the formation of the tubular insertion members and expulsion members include, without limitation, paperboard, cardboard, cup stock, paper, and the like. The applicators can be made by the following non-limiting processes: spiral winding as disclosed in U.S. Pat. No. 5,346,468, convolute winding as disclosed in U.S. Pat. No. 4,508,531, and forming a sheet around a mandrel and then sealing an overlapped seam as disclosed in U.S. Pat. No. 4,755,164.

The cardboard applicators may include a surface layer, which may be useful to increase the comfort and ease of insertion and withdrawal of the applicator. The surface layer may be in the form of laminated films, cured coatings, and the like. An example of such a surface layer is disclosed in co-pending application Ser. No. 09/105,787 filed on Jun. 26, 1998. A representative, non-limiting list of useful materials to be used as the surface layer includes, waxes, cellophane, polyolefins, polyesters, epoxies, and the like. The surface layers may also include thermal stabilizers, pigments, fragrances, surfactants, antimicrobial agents, medicaments, and the like. There are many techniques known for applying the surface layers. A representative, non-limiting list of such techniques includes spraying, extruding, slot-coating, brushing, transfer coating, and the like. Additional processing steps may be required to cure the surface treatments to a useable form, such as applying irradiation or other forms of energy.

Typical dimensions for each of the tubular insertion and expulsion members include a length of from about 50 to about 100 millimeters, a diameter of from about 8 to about 16 millimeters, and a thickness of from about 0.4 to about 0.6 millimeters. Preferably, the diameter of the expulsion member is less than the diameter of the tubular insertion member to allow for a telescopic arrangement of the two, as shown in FIG. 1.

The tubular insertion member of the applicator provided by the present invention is preferably substantially closed prior to expulsion of the materials contained therein. Alternatively, the insertion end of the applicator can be more or less open, that is the diameter in along the length of the tubular insertion member is substantially equivalent to the diameter of the insertion end. Proctor & Gamble, of Cincinnati, Ohio, currently offers for sale an open-ended tampon applicator under the trade name TAMPAX brand flushable applicator tampons. As can be seen in FIG. 1, one technique for substantially closing the insertion end of the applicator, is by employing a plurality of inwardly curved petals. The petals will flex and/or hinge to an open position upon expelling materials contained by the applicator. The number of petals generally ranges from about 4 to about 6. An alternative technique for substantially closing the insertion end of an applicator is by pleating the insertion end. This technique is disclosed in U.S. Pat. No. 5,782,793. When an applicator is constructed with more than one layer of material, a single layer may extend into the insertion end in an effort to reduce the force required to expel the contained materials. An example of this is disclosed in U.S. Pat. No. 5,827,214. These collective closures may be of spherical shape, or alternatively tapered shape.

Preferably the applicators provided by the present invention are cylindrical tubes that are substantially straight along their lengths, not including their gripper end. The applicators may however, be curvilinear to improve comfort and manipulation of the applicator during insertion and withdrawal from a body cavity. An example of a curved applicator can be seen in U.S. Pat. No. 5,158,535.

The applicator of the present invention can be used for the delivery of catemenial devices, such as tampons, intravaginal collection devices, and interlabial pads. The applicator may also be useful for delivery of oral, rectal, and vaginal suppositories, as well as nasal devices, such as nasal tampons. Further, the applicator can be used for delivery of various other materials including, medicaments, moisturizers, vitamins and minerals, spermicides, and odor controlling agents. These materials may be in the form of solids, creams, foams, gels, and the like.

The user may grasp the applicator and pivot the free end of the tab or tabs outwardly from the insertion member. The applicator is then inserted into the body cavity, and the contained material is expelled through the insertion end of the insertion member by forcing the expulsion member through its gripper end while bearing against the tab. To facilitate this expulsion, the user grasps the insertion member adjacent the outwardly pivoted tab or tabs with her manual digits that are disposed toward the insertion end, and she forces the expulsion member into the insertion member by the use of one or more additional manual digits. If the tab is in the form of a ring, she may insert a manual digit into the ring to bear against it during the expulsion of the contained material.

The disclosures of all patents, as well as any corresponding published foreign patent applications, mentioned throughout this patent application are hereby incorporated by reference herein.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. An applicator for delivering an object into a body cavity, comprising: an elongate insertion member having an insertion end; a gripper end opposite the insertion end; a length extending from the insertion end to the gripper end; an outer surface; and at least one tab pivotally connected to the elongate insertion member at a pivotal connection located proximal the gripper end, the at least one tab in a first position, as assembled, having an elevation that is substantially the same as that of the outer surface of the insertion member, the at least one tab having a fixed end disposed at the pivotal connection and a free end distal thereof, the free end being outwardly pivotable to a second position distal the applicator outer surface at the time of use to provide a bearing surface for one or more of a user's manual digits.

2. The applicator of claim 1 wherein the at least one tab has substantially similar elevation as portions of the elongate insertion member surrounding the at least one tab prior to use.

3. The applicator of claim 1 wherein at least two tabs are disposed about the gripper end.

4. The applicator of claim 3 wherein the at least two tabs are spaced substantially equally about the gripper end.

5. The applicator of claim 1 further comprising at least one protuberance adjacent the at least one tab fixed end, for restricting an angle of pivot of the at least one tab.

6. The applicator of claim 1 wherein the at least one tab fixed end comprises a region of weakness.

7. The applicator of claim 1 wherein the at least one tab is a ring, dimensioned and configured to accept at least a portion of one of a user's manual digits.

8. The applicator of claim 1 further comprising a region of weakness adjacent the at least one tab free end, wherein a portion of the elongate insertion member defined by the region of weakness can be inwardly displace.

9. The applicator of claim 8 wherein the region of weakness comprises one or more perforated lines.

10. The applicator of claim 1 wherein the elongate insertion member comprises paperboard.

11. The applicator of claim 1 wherein the elongate insertion member comprises plastic.

12. The applicator of claim 1 wherein the elongate insertion member outer surface comprises a polymeric material.

13. The applicator of claim 12 wherein the polymeric material comprises an epoxy.

14. The applicator of claim 1 further comprising an elongate expulsion member which is slideable within the elongate insertion member.

15. The applicator of claim 1 wherein the elongate insertion member is tubular.

16. The applicator of claim 1 wherein the tab is pivotable from an original orientation substantially parallel to the length of the applicator.

17. The applicator of claim 1 wherein the tab is pivotable from an original orientation substantially perpendicular to the length of the applicator.

18. An applicator for delivering an object into a body cavity, comprising: a tubular paperboard insertion member having a substantially closed insertion end; a gripper end opposite the insertion end; a length extending from the insertion end to the gripper end; an outer surface comprising a polymeric material; a plurality of tabs spaced about a circumference proximal the gripper end of the tubular paperboard insertion member, the tabs having a weakened fixed end and a free end capable of pivoting outwardly, wherein the tabs have substantially similar elevation as portions of the tubular paperboard insertion member surrounding the tabs prior to use; a region of weakness adjacent the tab free end, wherein a portion of the tubular paperboard insertion member defined by the region of weakness can be inwardly displaced; and an elongate expulsion member that is slideable within the tubular paperboard insertion member.

19. The applicator of claim 18 further comprising at least one protuberance adjacent the weakened fixed end, for restricting an angle of pivot of the tab.

20. The applicator of claim 18 wherein polymeric material comprises an epoxy.

21. A method of delivering materials into a mammalian body cavity comprising the steps of:
  a) grasping an applicator containing the material to be delivered, the applicator comprising
    i) an elongate insertion member having an insertion end; a gripper end opposite the insertion end; a length extending from the insertion end to the gripper end; an outer surface; and at least one tab pivotally connected to the elongate insertion member at a pivotal connection located proximal the gripper end, the at least one tab having a fixed end disposed at the pivotal connection and a free end distal thereof; and
    ii) an elongate expulsion member which is slideable within the elongate insertion member
  b) pivoting the free end of the at least one tab outwardly from insertion member;
  c) inserting at least the insertion end of the insertion member into the body cavity; and
  d) forcing the expulsion member through the gripper end of the insertion member while bearing against the at least one tab with at least one manual digit to expel the contained material through the insertion end of the insertion member and into the body cavity.

22. The method of claim 21 further comprising the steps of grasping the insertion member with at least two manual digits adjacent two outwardly pivoted tabs and disposed toward the insertion end of the insertion member and placing another manual digit on the expulsion member to force it through the gripper end of the insertion member.

23. The method of claim 21 wherein the at least one tab is a ring, dimensioned and configured to accept at least a portion of one of a user's manual digits.

24. The method of claim 23 further comprising the steps of inserting a manual digit through the ring and placing another manual digit on the expulsion member to force it through the gripper end of the insertion member.

25. An applicator for delivering an object into a body cavity, comprising: an elongate insertion member having an insertion end; a gripper end opposite the insertion end; a length extending from the insertion end to the gripper end; an outer surface; at least one tab pivotally connected to the elongate insertion member at a pivotal connection located proximal the gripper end; and at least one protuberance adjacent the at least one tab fixed end, for restricting an angle of pivot of the at least one tab, the at least one tab having a fixed end disposed at the pivotal connection and a free end distal thereof, the free end being outwardly pivotable to provide a bearing surface for one or more of a user's manual digits.

26. An applicator for delivering an object into a body cavity, comprising: an elongate insertion member having an insertion end; a gripper end opposite the insertion end; a length extending from the insertion end to the gripper end; an outer surface; at least one tab pivotally connected to the elongate insertion member at a pivotal connection located proximal the gripper end, the at least one tab having a fixed end disposed at the pivotal connection and a free end distal thereof, the free end being outwardly pivotable to provide a bearing surface for one or more of a user's manual digits; and a region of weakness adjacent the at least one tab free end, wherein a portion of the elongate insertion member defined by the region of weakness can be inwardly displaced.

* * * * *